(12) United States Patent
Buchholz et al.

(10) Patent No.: US 7,128,900 B2
(45) Date of Patent: Oct. 31, 2006

(54) LIGHT-PROTECTION AGENTS

(75) Inventors: Herwig Buchholz, Frankfurt (DE); Christophe Carola, Langen (DE); Sophie Perruchon, Wasselone (FR)

(73) Assignee: Merck Patent GmbH, Darmstadt (DE)

( * ) Notice: Subject to any disclaimer, the term of this patent is extended or adjusted under 35 U.S.C. 154(b) by 575 days.

(21) Appl. No.: 10/622,123

(22) Filed: Jul. 18, 2003

(65) Prior Publication Data
US 2004/0091433 A1    May 13, 2004

(30) Foreign Application Priority Data
Jul. 18, 2002    (DE) ................. 102 32 595

(51) Int. Cl.
*A61Q 17/00*    (2006.01)
*A61Q 17/04*    (2006.01)
*A61Q 19/00*    (2006.01)

(52) U.S. Cl. ................. 424/59; 424/60; 424/400; 424/401

(58) Field of Classification Search ................. 424/59, 424/60, 400, 401
See application file for complete search history.

(56) References Cited

U.S. PATENT DOCUMENTS 5,889,003 A * 3/1999 Dhainaut et al. ........ 514/233.5

* cited by examiner

*Primary Examiner*—Shelley A. Dodson
(74) *Attorney, Agent, or Firm*—Millen White Zelano & Branigan, P.C.

(57) ABSTRACT

The invention relates to a preparation having light-protection properties comprising at least one compound of the formula I

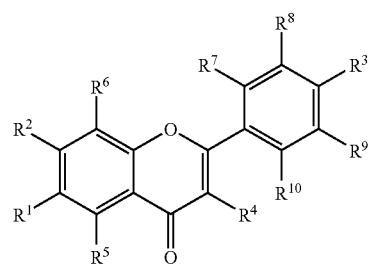

where $R^1$ and $R^2$ are selected from H and $OR^{11}$, where each $OR^{11}$, independently of the others, is OH, a straight-chain or branched $C_1$- to $C_{20}$-alkoxy group, a straight-chain or branched $C_3$- to $C_{20}$-alkenyloxy group, a straight-chain or branched $C_1$- to $C_{20}$-hydroxyalkoxy group, where the hydroxyl group(s) may be bonded to a primary or secondary carbon atom in the chain and furthermore the alkyl chain may also be interrupted by oxygen, and/or a $C_3$- to $C_{10}$-cycloalkoxy group and/or $C_3$- to $C_{12}$-cyclo-alkenyloxy group, where the rings may each also be bridged by $-(CH_2)_n-$ groups, where n=1 to 3, and/or a mono- and/or oligoglycosyl radical, with the proviso that at least one radical from $R^1$ and $R^2$ is $OR^{11}$, and $R^3$ is a radical $OR^{11}$, and $R^4$ to $R^7$ and $R^{10}$ may be identical or different and are, independently of one another, radicals which are substantially inert with respect to the UV properties.

19 Claims, 4 Drawing Sheets

LIGHT-PROTECTION AGENTS

The present invention relates to a preparation having light-protection properties and to the preparation and use thereof.

A certain degree of tanning of the skin is regarded in modern society as attractive and as an expression of vigour and sportiness. In addition to this desired action of the sun on the skin, a number of undesired side effects occur, such as sunburn or premature skin ageing and wrinkling. A number of effective UV filters have now been developed which, applied to the skin in the form of creams, lotions or gels, are able effectively to prevent the development of sunburn, even in the case of relatively great exposure to the sun. The UV filters present in the pharmaceutical or cosmetic preparation form a film or layer on the surface of the skin and do not penetrate into deeper skin layers with further care substances present in the preparation. Known UV filters and sunscreens thus only act by absorbing certain regions of the sunlight, thus preventing this radiation from penetrating into deeper layers of the skin. As is known, the most dangerous part of solar radiation is formed by ultraviolet rays having a wavelength of less than 400 nm. The lower limit for the ultraviolet rays which reach the earth's surface is restricted to about 280 nm by absorption in the ozone layer. The sun-protection filters usual today in cosmetics absorb in a wavelength range from 280 to 400 nm. This range covers UV-B rays having a wavelength of between 280 and 320 nm, which play a crucial role in the formation of solar erythema, and also UV-A rays having a wavelength of between 320 and 400 nm, which tan the skin, but also allow ageing, favor the triggering of an erythematous reaction or can exacerbate this reaction in certain people or even trigger phototoxic or photoallergic and irritative reactions.

Skin damage is not caused just by sunlight, but also by other external influences, such as cold or heat. Furthermore, the skin undergoes natural ageing, with the formation of wrinkles and a reduction in the elasticity of the skin.

The object of care cosmetics is wherever possible to obtain the impression of youthful skin. In principle, there are various ways of achieving this object. For example, existing skin damage, such as irregular pigmentation or the development of wrinkles, can be compensated for by covering powders or creams. Another approach is to protect the skin against environmental influences which lead to permanent damage and thus ageing of the skin. The idea is therefore to intervene in a preventative manner and thus to delay the ageing process. One example of this is the UV filters already mentioned, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening defence functions of the skin against harmful influences with increasing age by externally supplying substances which are able to replace this diminishing defence or repair function. For example, the skin has the ability to scavenge free radicals formed by external or internal stress factors. This ability diminishes with increasing age, causing the ageing process to accelerate with increasing age.

A further difficulty in the preparation of cosmetics is that active ingredients which are intended to be incorporated into cosmetic preparations are frequently unstable and can be damaged in the preparation. The damage may be caused, for example, by a reaction with atmospheric oxygen or by absorption of UV rays. The molecules damaged in this way may, for example, change their color and/or lose their activity through their structural change.

The more recent literature contains various suggestions for solving the said problems:

DE 197 46 654 A1 describes cosmetic and pharmaceutical preparations comprising photostable UV filters. 4,4-Diarylbutadienes are used here as photostable UV filters in cosmetic and pharmaceutical preparations for protecting the human skin or human hair against sunlight, alone or together with compounds which absorb in the UV region and which are known per se for cosmetic and pharmaceutical preparations.

DE 195 08 608 A1 describes a light-stable cosmetic composition. Cosmetic compositions are disclosed for protection against UV rays having a wavelength of between 280 and 400 nm which comprise at least one tetraalkylquercetin in a cosmetically acceptable, oil-based medium.

DE 197 55 504 A1 describes the use of flavones and flavonoids against UV-induced decomposition of dibenzoylmethane and its derivatives.

WO 02/00214 describes the use of certain flavone derivatives for the preparation of oral medicaments for the systemic treatment and prophylaxis of UV-induced dermatosis, in particular of polymorphic light dermatosis and its subforms, and/or undesired long-term consequences of UV irradiation, particularly light ageing. Preferred flavone derivatives here are, in particular, naturally occurring bioflavonoids, such as rutin, naringin, naringenin, hesperidin, hesperetin, taxifolin, etc., and derivatives thereof, such as troxerutin and monoxerutin.

European Patent Application EP-A-1 147 764 describes cosmetic compositions which comprise up to 10% by weight of polymethoxyflavones having at least four methoxy functions. Advantages of this composition are a skin-lightening effect in combination with prevention of wrinkles as well as storage stability and safety on use.

International Patent Application WO 00/61095 describes mixtures of polyphenols with vitamins. These mixtures are suitable for use in cosmetic or dermatological compositions and are optimized for scavenging free radicals, such as hydroxyl free radicals or peroxides. Particular preference is given here to the combination of troxerutin with α-tocopherol succinate and ascorbyl palmitate.

However, there continues to be a demand for skin-tolerated UV filters which are also suitable for use in skin-care preparations.

The object of the invention is therefore to provide a composition which has a protective action against UV rays and/or exerts a protective action against oxidative stress on body cells and/or counters skin ageing.

Surprisingly, it has been found that certain flavonoids are highly suitable as UV filters. The present invention therefore firstly relates to preparations comprising these flavonoids.

This object is achieved by a preparation having light-protection properties comprising at least one compound of the formula I

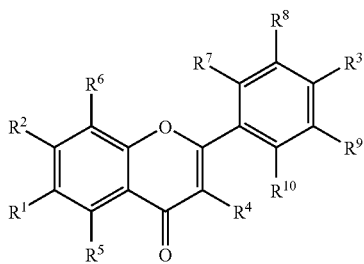

where $R^1$ and $R^2$ are selected from

H and $OR^{11}$, where each $OR^{11}$, independently of the others, is

OH, a straight-chain or branched $C_1$- to $C_{20}$-alkoxy group, a straight-chain or branched $C_3$- to $C_{20}$-alkenyloxy group, a straight-chain or branched $C_1$-to $C_{20}$-hydroxyalkoxy group, where the hydroxyl group(s) may be bonded to a primary or secondary carbon atom in the chain and the alkyl chain may optionally be interrupted by oxygen, and/or a $C_3$- to $C_{10}$-cycloalkoxy group and/or $C_3$- to $C_{12}$-cyclo-alkenyloxy group, where the rings may each also be bridged by —$(CH_2)_n$— groups, where n=1 to 3, and/or a mono- and/or oligoglycosyl radical, with the proviso that at least one radical from $R^1$ and $R^2$ is $OR^{11}$, and $R^3$ is a radical $OR^{11}$, and $R^4$ to $R^7$ and $R^{10}$ may be identical or different and are, independently of one another,

H, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and the alkyl chain may optionally be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, and $R^8$ and $R^9$ may be identical or different and are, independently of one another,

H, $OR^{11}$, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom in the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3.

Advantages of the compositions according to the invention are, in particular, the UV light-filtering action and the fact that they are well tolerated by the skin. In addition, the compounds described here are colorless or only weakly colored and thus, in contrast to many known naturally occurring flavonoids, do not result in discoloration of the preparations.

The present invention therefore furthermore relates to the use of the compounds of the formula I, as indicated above, as UV filters or for the preparation, of a preparation having light-protection properties.

The preparations are usually preparations which can be applied topically, for example cosmetic or dermatological formulations. In this case, the preparations comprise a cosmetically or dermatologically suitable excipient and, depending on the desired property profile, optionally further suitable ingredients.

The flavonoids of the formula I to be employed in accordance with the invention include broad-band UV filters, which can be employed alone or in combination with further UV filters.

Other compounds of the formula I which are likewise preferred exhibit an absorption maximum in the transition region between UV-B and UV-A radiation. As UV-A-II filters, they therefore advantageously supplement the absorption spectrum of commercially available UV-B and UV-A-I filters.

Preferred preparations according to the invention having light-protection properties comprise at least one compound of the formula I in which $R^3$ is OH or straight-chain or branched $C_1$- to $C_{20}$-alkoxy groups, preferably methoxy, ethoxy or ethylhexyloxy, or mono- and/or oligoglycosyl radicals, preferably glucosyl radicals, and $R^1$ and/or $R^2$ are preferably OH or straight-chain or branched $C_1$- to $C_{20}$-alkoxy groups, preferably methoxy, ethoxy or ethylhexyloxy, or mono- and/or oligoglycosyl radicals, preferably mono- or oligosaccharides, more preferably glucosyl radicals.

These preferred compounds are distinguished by particularly strong UV absorption.

In addition, preferred compounds of this type have advantages on incorporation into the preparations:

mono- and/or oligoglycosyl radicals improve the water solubility of the compounds to be employed in accordance with the invention;

straight-chain or branched $C_1$- to $C_{20}$-alkoxy groups, in particular long-chain alkoxy functions, such as ethylhexyloxy groups, increase the oil solubility of the compounds;

i.e. the hydrophilicity or lipophilicity of the compounds according to the invention can be controlled via a suitable choice of substituents.

Preferred mono- or oligosaccharide radicals are hexosyl radicals, in particular ramnosyl radicals and glucosyl radicals. However, other hexosyl radicals, for example allosyl, altrosyl, galactosyl, gulosyl, idosyl, mannosyl and talosyl, may also advantageously be used. It may also be advantageous to use pentosyl radicals. The glycosyl radicals may be linked to the basic structure by means of an α- or β-glycosidic link. A preferred disaccharide is, for example, 6-O-(6-deoxy-α-L-mannopyranosyl)-β-D-glucopyranoside.

However, in likewise preferred embodiments of the invention, the preparations according to the invention may also contain compounds of the formula I which are insoluble or have low solubility in the preparation matrix. In this case, the compounds are preferably dispersed in the cosmetic preparation in finely divided form.

According to previous knowledge, the radicals $R^4$ to $R^7$ and $R^{10}$ have only an insignificant effect on the desired molar UV absorption and are therefore, for the purposes of the present invention, to be regarded as substantially inert with respect to UV absorption. However, since the absorption per gram of substance is important for the preparation, preference is given in accordance with the invention to preparations which comprise at least one compound of the formula I which is characterized in that $R^4$ to $R^7$ and $R^{10}$ are H.

It has been found that the intensity of UV absorption is particularly high if $R^3$ is a straight-chain or branched $C_1$- to $C_{20}$-alkoxy group, preferably methoxy, ethoxy or ethylhexyloxy, and $R^8$ and $R^9$ are identical and are H or straight-chain or branched $C_1$-to $C_{20}$-alkoxy groups, preferably methoxy, ethoxy or ethylhexyloxy. In accordance with the invention, particular preference is therefore given to preparations having light-protection properties comprising at least one compound of the formula I which is characterized in that $R^3$ is a straight-chain or branched $C_1$- to $C_{20}$-alkoxy group, preferably methoxy, ethoxy or ethylhexyloxy, and $R^8$ and $R^9$ are identical and are H or straight-chain or branched $C_1$-to $C_{20}$-alkoxy groups, preferably methoxy, ethoxy or ethylhexyloxy. $R^8$ and $R^9$ here are particularly preferably H.

The compounds of the formula I are typically employed in accordance with the invention in amounts of from 0.01 to 20% by weight, preferably in amounts of from 0.5% by weight to 10% by weight and particularly preferably in amounts of from 1 to 8% by weight. The person skilled in the art is presented with absolutely no difficulties in selecting the amounts correspondingly depending on the intended light protection factor of the preparation.

Preparations which are particularly preferred in accordance with the invention comprise, as stated above, further UV filters, preferably UV-B and UV-A-I filters, besides the compounds of the formula I.

On use of the dibenzoylmethane derivatives which are particularly preferred as UV-A filters in combination with the compounds of the formula I, an additional advantage arises: the UV-sensitive dibenzoylmethane derivatives are addition ally stabilized by the presence of the compounds of the formula I. The present invention therefore furthermore relates to the use of the compounds of the formula I for the stabilisation of dibenzoylmethane derivatives in preparations.

In principle, all UV filters are suitable for combination with the compounds of the formula I according to the invention. Particular preference is given to UV filters whose physiological acceptability has already been demonstrated. Both for UVA and UVB filters, there are many proven substances which are known from the specialist literature, for example:

Benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL);

Benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020);

Benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40);

Methoxycinnamic acid esters, such as octyl methoxycinnamate (for example Eusolex® 2292), isopentyl 4-methoxycinnamate, for example as a mixture of the isomers (for example Neo Heliopan® E 1000);

Salicylate derivatives, such as 2-ethylhexyl salicylate (for example Eusolex® OS), 4-isopropylbenzyl salicylate (for example Megaso®l) or 3,3,5-trimethylcyclohexyl salicylate (for example Eusolexe® HMS);

4-aminobenzoic acid and derivatives, such as 4-aminobenzoic acid, 2-ethylhexyl 4-(dimethylamino)benzoate (for example Eusolexe 6007) or ethoxylated ethyl 4-aminobenzoate (for example Uvinul® P25);

Phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopane AP) or 2,2-(1,4-phenylene)bisbenzimidazole-6-sulfonic acid;

and further substances, such as
2-ethylhexyl 2-cyano-3,3-diphenylacrylate (for example Eusolex® OCR),
3,3'-(1,4-phenylenedimethylene)bis(7,7-dimethyl-2-oxobicyclo[2.2.1]hept-1-ylmethanesulfonic acid and salts thereof (for example Mexoryl® SX),
2,4,6-trianilino-(p-carbo-2'-ethylhexyl-1'-oxy)-1,3,5-triazine (for example Uvinul® T 150) and
hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

These organic UV filters are generally incorporated into cosmetic formulations in an amount of from 0.5 to 10 percent by weight, preferably 1–8%.

Further suitable organic UV filters are, for example,
2-(2H-benzotriazol-2-yl)-4-methyl-6-(2-methyl-3-(1,3,3,3-tetramethyl-1 (trimethylsilyloxy)disiloxanyl)propyl) phenol (for example Silatrizole®),
2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB),
α-(trimethylsilyl)-ω-[trimethylsilyl)oxy]poly[oxy(dimethyl [and about 6% of methyl[2-[p-[2,2-bis(ethoxycarbonyl]vinyl]phenoxy]-1-methyleneethyl] and approximately 1.5% of methyl[3-[p-[2,2-bis(ethoxycarbonyl)vinyl]phenoxy]propenyl] and from 0.1 to 0.4% of (methylhydrogen]silylene]] (n≈60) (CAS No. 207 574-74-1)
2,2'-methylenebis(6-(2H-benzotriazol-2-yl)-4-(1,1,3,3-tetramethylbutyl)phenol) (CAS No. 103 597-45-1)
2,2'-(1,4-phenylene)bis(1H-benzimidazole-4,6-disulfonic acid, mono-sodium salt) (CAS No. 180 898–37–7) and
2,4-bis{[4-(2-ethylheyloxy)-2-hydroxy]phenyl}-6-(4-methoxyphenyl)-1,3,5-triazine (CAS No. 103 597-45-, 187 393-00-6).

Organic UV filters are generally incorporated into cosmetic formulations in an amount of from 0.5 to 20 percent by weight, preferably 1–15%.

Conceivable inorganic UV filters are those from the group consisting of titanium dioxides, such as, for example, coated titanium dioxide (for example Eusolex® T-2000, Eusolex®

T-AQUA), zinc oxides (for example Sachtotec®), iron oxides and also cerium oxides. These inorganic UV filters are generally incorporated into cosmetic preparations in an amount of from 0.5 to 20 percent by weight, preferably 2–10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxy-benzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and triethanolamine salts.

The protective action against the damaging effects of UV radiation can be optimized by combining one or more compounds of the formula I with further UV filters.

Optimized compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters and the compounds of the formula I can also be employed in encapsulated form. In particular, it is advantageous to employ organic UV filters in encapsulated form. In detail, the following advantages arise:

- The hydrophilicity of the capsule wall can be set independently of the solubility of the UV filter. Thus, for example, it is also possible to incorporate hydrophobic UV filters into purely aqueous preparations. In addition, the oily impression on application of the preparation comprising hydrophobic UV filters, which is frequently regarded as unpleasant, is suppressed.
- Certain UV filters, in particular dibenzoylmethane derivatives, exhibit only reduced photostability in cosmetic preparations. Encapsulation of these filters or compounds which impair the photostability of these filters, such as, for example, cinnamic acid derivatives, enables the photostability of the entire preparation to be increased.
- Skin penetration by organic UV filters and the associated potential for irritation on direct application to the human skin is repeatedly being discussed in the literature. The encapsulation of the corresponding substances which is proposed here suppresses this effect.
- In general, encapsulation of individual UV filters or other ingredients enables preparation problems caused by the interaction of individual preparation constituents with one another, such as crystallisation processes, precipitation and agglomerate formation, to be avoided since the interaction is suppressed.

It is therefore preferred in accordance with the invention for one or more of the compounds of the formula I or the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by sol-gel processes, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in preparations according to the invention are preferably present in amounts which ensure that the encapsulated UV filters are present in the preparation in the above-indicated amounts.

If the compounds to be employed in accordance with the invention have free hydroxyl groups, they additionally exhibit, in addition to the properties described, an action as antioxidant and/or free-radical scavenger. Preference is therefore also given to preparations having light-protection properties comprising at least one compound of the formula I which is characterized in that at least one of the radicals $R^1$ to $R^3$ is OH, where preferably at least one of the radicals $R^1$ and $R^2$ is OH.

In order that the compounds of the formula I are able to develop their positive action as free-radical scavengers on the skin particularly well, it may be preferred to allow the compounds of the formula I to penetrate into deeper skin layers. Several possibilities are available for this purpose. Firstly, the compounds of the formula I can have an adequate lipophilicity in order to be able to penetrate through the outer skin layer into epidermal layers. As a further possibility, corresponding transport agents, for example liposomes, which enable transport of the compounds of the formula I through the outer skin layers may also be provided in the preparation. Finally, systemic transport of the compounds of the formula I is also conceivable. The preparation is then designed, for example, in such a way that it is suitable for oral administration.

The substances of the formula I act as free-radical scavengers. Free radicals of this type are not generated only by sunlight, but are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leucocytes, but also associated with the formation (through disproportionation in the presence of iron(II) ions) of the hydroxyl free radicals and other reactive species which are normally involved in the phenomenon of phagocytosis; and lipid autooxidation, which is generally initiated by a hydroxyl free radical and produces lipidic alkoxy free radicals and hydroperoxides.

The preferred compounds of the formula I also act as enzyme inhibitors. They inhibit histidine decarboxylase, protein kinases, elastase, aldose reductase and hyalurohidase, and therefore enable the intactness of the basic substance of vascular sheaths to be maintained. Furthermore, they inhibit non-specifically catechol O-methyl transferase, causing the amount of available catecholamine and thus the vascular strength to be increased. Furthermore, they inhibit AMP phosphodiesterase, giving the substances effectiveness for inhibiting thrombocyte aggregation. Owing to these properties, the preparations according to the invention are suitable for immune protection and for the protection of DNA and RNA. In particular, the preparations are suitable for the protection of DNA and RNA against oxidative attack, against free radicals and against damage due to radiation, in particular UV radiation. A further advantage of the preparations according to the invention is cell protection, in particular protection of Langerhans cells against damage due to the above-mentioned influences. All these uses and the use of the compounds of the formula I for the preparation of preparations which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leucoplasia, leucoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopia, such as eczema or respiratory atopia, or hypertrophy of the gums, it furthermore being possible for the compounds to be used for some inflammations which are not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophia of the epidermis and/or dermis caused by locally or systemically applied corticosteroids and all other types of skin atrophia, for the prevention or treatment of defects in wound healing, for the prevention or elimination of stretch marks caused by pregnancy or for the promotion of wound healing, for combating defects in tallow production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

The protective action against oxidative stress or against the effect of free radicals can be further improved if the preparations comprise one or more further antioxidants.

In a preferred embodiment of the present invention, the preparation is therefore a preparation for the protection of body cells against oxidative stress, in particular for reducing skin ageing, characterized in that it preferably comprises one or more antioxidants.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynee K LIQUID), to copherol extracts from natural sources, L(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L(+)-ascorbyl palmitate and citric acid (for example Oxynex® 2004). Antioxidants of this type are usually employed with compounds of the formula I in compositions of this type in ratios in the range from 1000:1 to 1:1000, preferably in amounts of from 100:1 to 1:100.

The preparations according to the invention may comprise vitamins as further ingredients. The cosmetic preparations according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C, DL-α-tocopherol, tocopherol E acetate, nicotinic acid, pantothenic acid and biotin. Vitamins are usually employed here with compounds of the formula I in ratios in the range from 1000:1 to 1:1000, preferably in amounts of from 100:1 to 1:100.

The preparations according to the invention may in addition comprise further conventional skin-protecting or skin-care active ingredients. These may in principle be any active ingredients known to the person skilled in the art.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.*, 149 (1985) pages 135–139). Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof. These compounds stabilize enzymes and other biomolecules in aqueous solutions and organic solvents. Furthermore, they stabilize, in particular, enzymes against denaturing conditions, such as salts, extreme pH values, surfactants, urea, guanidinium chloride and other compounds.

Ectoin and ectoin derivatives, such as hydroxyectoin, can advantageously be employed in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacteria cells. Pharmaceutical products, such as non-glycosylated, pharmaceutically active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European Patent Application EP-A-0 671 161 describes, in particular, that ectoin and hydroxyectoin are employed in cosmetic preparations, such as powders, soaps, surfactant-containing cleansing products, lipsticks, rouge, make-ups, care creams and sunscreen preparations.

Preference is given here to the use of a pyrimidinecarboxylic acid of the following formula II

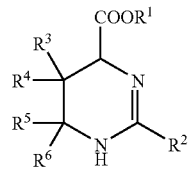

II in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group consisting of H, OH, $NH_2$ and $C_{1-4}$-alkyl. Preference is given to the use of pyrimidinecarboxylic acids in which $R^2$ is a methyl or ethyl group, and $R^1$ or $R^5$ and $R^5$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). The preparations according to the invention preferably comprise pyrimidinecarboxylic acids of this type in amounts of up to 15% by weight. The pyrimidinecarboxylic acids are preferably employed here in ratios of from 100:1 to 1:100 with respect to the compounds of the formula I, with ratios in the range from 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Preparations which comprise 2-hydroxy-5-methyllaurophenone oxime are accordingly suitable for the treatment of skin diseases which are accompanied by inflammation. It is known that preparations of this type can be used, for example, for the therapy of psoriasis, various forms of eczema, irritative and toxic dermatitis, UV dermatitis and further allergic and/or inflammatory diseases of the skin and integumentary appendages. Preparations according to the invention which, in addition to the compound of the formula I, additionally comprise an aryl oxime, preferably 2-hydroxy-5-methyllaurophenone oxime, exhibit surprising antiinflammatory suitability. The preparations here preferably comprise from 0.01 to 10% by weight of the aryl oxime, it being particularly preferred for the preparation to comprise from 0.05 to 5% by weight of aryl oxime.

All compounds or components which can be used in the preparations are either known or are commercially available or can be synthesised by known processes.

The one or more compounds of the formula I can be incorporated into cosmetic preparations in the customary manner. Suitable preparations are those for external use, for example in the form of a cream, lotion or gel or as a solution which can be sprayed onto the skin. Suitable for internal use are administration forms such as capsules, coated tablets, powders, tablet solutions or solutions.

Examples which may be mentioned of application forms of the preparations according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any desired customary excipients, auxiliaries and, if desired, further active ingredients may be added to the preparation.

Preferred auxiliaries originate from the group consisting of preservatives, antioxidants, stabilizers, solubilizers, vitamins, colorants and odor improvers.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubilisers and emulsifiers, for example water, ethanol, isopropanol, ethyl carbonate, ethyl acetate, benzyl alcohol, benzyl benzoate, propylene glycol, 1,3-butylglycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary excipients, such as liquid diluents, for example water, ethano or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary excipients, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic application forms are also lipsticks, lip-care sticks, mascara, eyeliner, eye-shadow, rouge, powder make-up, emulsion make-up and wax make-up, and sunscreen, pre-sun and after-sun preparations.

The preferred preparation forms according to the invention include, in particular, emulsions.

Emulsions according to the invention are advantageous and comprise, for example, the said fats, oils, waxes and other fatty substances, as well as water and an emulsifier, as usually used for a preparation of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, or from the group consisting of esters of aromatic carboxylic acids and saturated and/or unsaturated, branched and/or unbranched alcohols having a chain length of from 3 to 30 carbon atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated and unsaturated, branched and unbranched alcohols, and fatty acid triglycerides, specifically the triglycerol esters of saturated and/or unsaturated, branched and/or unbranched alkanecarboxylic acids having a chain length of from 8 to 24, in particular 12–18, carbon atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyidodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageousiare mixtures of cyclomethicone and isotridecyl isononanoate and of cyclomethicone and 2-ethylhexyl isostearate.

The aqueous phase of the preparations according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the preparations according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylgluosides which are distinguished by the structural formula

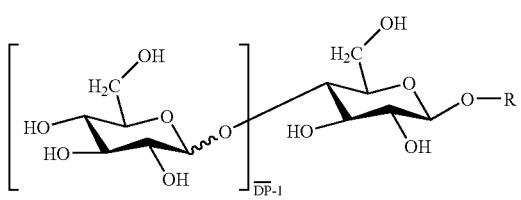

where R is a branched or unbranched alkyl radical having from 4 to 24 carbon atoms, and where $\overline{DP}$ denotes a mean degree of glucosidation of up to 2.

The value $\overline{DP}$ represents the degree of glucosidation of the alkyl-glucosides used in accordance with the invention and is defined as $$\overline{DP} = \frac{p_1}{100} \cdot 1 + \frac{p_2}{100} \cdot 2 + \frac{p_2}{100} \cdot 3 + \ldots = \Sigma \frac{p_i}{100} \cdot i$$

in which $p_1, p_2, p_3, \ldots p_i$ represent the proportion of mono-, di-, tri- . . . i-fold glucosylated products in percent by weight. Advantageous according to the invention are products having degrees of glucosidation of 1-2, particularly advantageously of from 1.1 to 1.5, very particularly advantageously of 1.2–1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40–70% by weight, is advantageous in accordance with the invention.

Alkylglucosides which are particularly advantageously used for the purposes of the invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantarene® 1200 (Henkel KGaA), Oramix® NS 10 (Seppic).

The acyllactylates are themselves advantageously selected from the group consisting of the substances which are distinguished by the structural formula

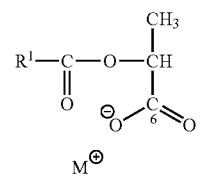

where $R^1$ is a branched or unbranched alkyl radical having from 1 to 30 carbon atoms, and $M^+$ is selected from the group consisting of the alkali metal ions and the group consisting of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formula

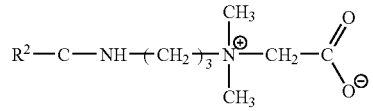

where $R^2$ is a branched or unbranched alkyl radical having from 1 to 30 carbon atoms.

$R^2$ is particularly advantageously a branched or unbranched alkyl radical having from 6 to 12 carbon atoms.

For example, capramidopropylbetaine, for example the product Tego® Betain 810 from Th. Goldschmidt AG, is advantageous.

A coconut amphoacetate which is advantageous for the purposes of the invention is, for example, sodium coconut amphoacetate, as available under the name Miranol® Ultra C32 from Miranol Chemical Corp.

The preparations according to the invention are advantageously characterized in that the hydrophilic surfactant(s) is (are) present in concentrations of 0.01–20% by weight, preferably 0.05–10% by weight, particularly preferably 0.1–5% by weight, in each case based on the total weight of the composition.

For use, the cosmetic and dermatological preparations according to the invention are applied to the skin and/or the hair in an adequate amount in the usual manner for cosmetics.

Cosmetic and dermatological preparations according to the invention may exist in various forms. Thus, they may be, for example, a solution, a water-free preparation, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favorable. Preference is given to emulsions. O/W emulsions are particularly preferred. Emulsions, W/O emulsions and O/W emulsions are obtainable in a conventional manner.

Emulsifiers that can be used are, for example, the known W/O and O/w emulsifiers. It is advantageous to use further conventional co-emulsifiers in the preferred O/W emulsions according to the invention.

Co-emulsifiers which are advantageous according to the invention are, for example, O/W emulsifiers, principally from the group consisting of the substances having HLB values of 11–16, very particularly advantageously having HLB values of 14.5–15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

The ethoxylated alkyl ether carboxylic acid or salt thereof used can advantageously be sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favorable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageous for the purposes of the invention are the following:

fatty alcohols having from 8 to 30 carbon atoms, monoglycerol esters of saturated and/or unsaturated, branched and/or unbranched alkanecarboxylic acids having a chain length of from 8 to 24 carbon atoms, in particular 12–18 carbon atoms, diglycerol esters of saturated and/or unsaturated, branched and/or unbranched alkanecarboxylic acids having a chain length of from 8 to 24 carbon atoms, in particular 12–18 carbon atoms, monoglycerol ethers of saturated and/or unsaturated, branched and/or unbranched alcohols having a chain length of from 8 to 24 carbon atoms, in particular 12–18 carbon atoms, diglycerol ethers of saturated and/or unsaturated, branched and/or unbranched alcohols having a chain length of from 8 to 24 carbon atoms, in particular 12–18 carbon atoms, propylene glycol esters of saturated and/or unsaturated, branched and/or unbranched alkanecarboxylic acids having a chain length of from 8 to 24 carbon atoms, in particular 12–18 carbon atoms, and sorbitan esters of saturated and/or unsaturated, branched and/or unbranched alkanecarboxylic acids having a chain length of from 8 to 24 carbon atoms, in particular 12–18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

The preferred preparations according to the invention are particularly suitable for protecting human skin against ageing processes and against oxidative stress, i.e. against damage caused by free radicals, as are produced, for example, by solar irradiation, heat or other influences. In this connection, it is in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments which color the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are generally used.

The cosmetic preparation may also be used to protect the hair against photochemical damage in order to prevent color changes, bleaching or damage of a mechanical nature: In this case, a suitable formulation is in the form of a rinse-out shampoo, lotion, gel or emulsion, the preparation in question being applied before or after shampooing, before or after coloring or bleaching or before or after permanent waving. It is also possible to select a preparation in the form of a lotion or gel for styling or treating the hair, in the form of a lotion or gel for brushing or blow-waving, in the form of a hair lacquer, permanent waving composition, colorant or bleach for the hair. Besides the compounds of the formula I, the preparation having light-protection properties may comprise various adjuvants used in this type of composition, such as surfactants, thickeners, polymers, softeners, preservatives, foam stabilizers, electrolytes, organic solvents, silicone derivatives, oils, waxes, antigrease agents, dyes and/or pigments which color the composition itself or the hair, or other ingredients usually used for hair care.

The present invention furthermore relates to a process for the preparation of a preparation which is characterized in that at least one compound of the formula I having radicals as described above is mixed with a cosmetically or dermatologically suitable-excipient, and to the use of a compound of the formula I for the preparation of a preparation having light-protection properties.

The preparations according to the invention can be prepared using techniques which are well known to the person skilled in the art.

The mixing can result in dissolution, emulsification or dispersion of the compound of the formula I in the excipient.

In a process which is preferred in accordance with the invention, the compound of the formula I is prepared by reacting a 2-hydroxyacetophenone compound with a lithium compound and subsequently with a keto compound.

For example, as described by M. Cushman and D. Nagarathnam in: Tetrahedron Letters, 31, 6497–6500, 1990 and M. Cushman; D. Nagarathnam; Journal of Organic Chemistry, 56, 4884–4887, 1991, the phenolic hydroxyl groups can be deprotonated using a large excess of lithium bis (trimethylsilyl)amide under homogeneous reaction conditions in order to prepare the lithium enolate of the corresponding ketone. The carbon atom of the lithium enolate can subsequently be acylated regioselectively using an aroyl chloride to give a β-diketone intermediate directly, which is subsequently cyclised in the acidic medium. However, this process has the disadvantage of the large excess of lithium base, which can only be removed with difficulty, even in a plurality of purification steps, and the high price of the lithium base.

It is therefore particularly preferred to carry out a process as described in the earlier international patent application with the filing reference 02/00233. In this process, which is preferred in accordance with the invention, the ratio between the molar equivalents of lithium compound and the molar equivalents of 2-hydroxyacetophenone compound functional groups to be metallated is selected in the range from 1 to 1.2.

Surprisingly, it has been found that the above-mentioned ratio allows complete metallation of all hydroxyl groups and the carbonyl group of the 2-hydroxyacetophenone compound. A ratio of less than 1 would result in incomplete metallation and thus in a large number of undesired by-products. A ratio of more than 1.2, by contrast, means the use of a larger amount of the lithium compounds, which are usually not inexpensive, and the entrainment of lithium compounds in all further subsequent steps, in particular purification steps.

The lithium compound is preferably selected from inorganic lithium compounds, since they are available inexpensively and readily in large amounts. Furthermore, they offer the advantage that they are sparingly soluble to insoluble in organic solvents, meaning that, if employed in excess, they can easily be filtered out of the reaction mixture after a metallation reaction carried out under heterogeneous conditions.

In a preferred embodiment of the process according to the invention, the ratio between the lithium compound and the 2-hydroxyacetophenone compound functional groups to be metallated is precisely 1. It is thus achieved that no lithium compounds that may still be dissolved occur as impurities in the end product, since these usually cannot be removed from the intermediates and end products, even by purification steps, such as recrystallisation.

The metallation is advantageously carried out in an ethereal solvent, since this supports the metallation reaction through its polarity through the formation of Li solvates, increasing the basicity of the lithium base.

The 2-hydroxyacetophenone employed in the process according to the invention preferably has the following structure:

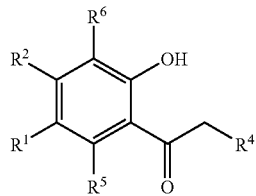

where $R^1$, $R^2$ and $R^4$ to $R^6$ are as defined above or are groups which can be converted into groups as defined above by chemical modifications, such as, for example, removal of protecting groups, oxidation or reduction.

The keto compound for carrying out the process according to the invention preferably has the following structure:

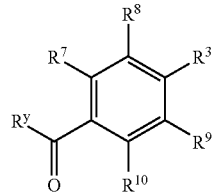

where $R^3$ and $R^7$ to $R^{10}$ are as defined above or are groups which can be converted into groups as defined above by chemical modifications, such as, for example, removal of protecting groups, oxidation or reduction, and where Ry can be a halide, alkoxy or ester group.

The hydroxyl groups of the 2-hydroxyacetophenone compound are preferably not protected. Complex reactions for introduction and removal of protecting groups are thus avoided, enabling the reaction to proceed particularly simply.

In the case of the keto compounds, $R^y$ is chloride, i.e. the compound is an acid chloride, an alkoxy group, i.e. the compound is an ester, or an ester group, i.e. the compound is an acid anhydride. The use of different groups also enables variation and precise selection of the reaction time, depending on the substrate employed. For example, the reaction time on use of an acid chloride or acid anhydride is between 2 and 6 hours, usually between 4 and 5 hours. On use of an ester or on use of silylated protecting groups, the reaction time is more than 8 hours, usually more than 10 hours, but often also about 16–20 hours.

Firstly, the 2-hydroxyacetophenone compound is preferably condensed with the ketone and a lithium compound in dry THF at low temperatures (from −78° C. to −50° C.), giving a stable diketone intermediate. At temperatures above −50° C., the reaction either does not proceed at all or does so too quickly, i.e. with undesired by-products or alternatively with decomposition of the starting material, so that the range from −78° C. to −50° C. is preferred. The diketone is subsequently cyclised at 95–100° C. under acidic conditions, to give a flavone derivative.

Particularly suitable lithium bases which are used in the process according to the invention are the lithium bases listed below:

$LiNH_2$, $LiN(CH_3)_2$, $LiN(C_2H_5)_2$, $LiNCH(CH_3)_2$ (LDA), $Me_3CLi$, $PhCH_2Li$, $Ph_2CHLi$, $Ph_3CLi$, $LiCN$, $LiC(NO_3)_3$, $LiC(CN)_3$, $LiN(C_6H_{11})_2$, $LiN(CH_2)_2$, $LiCH_3$, $LiC_2H_5$, $LiCH(CH_3)_2$, $LiC_4H_9$, $LiCH_2CH(CH_3)_2$, $LiC_6H_{13}$, $LiPh$, $LiCH_3COCHCOCH_3$, $LiClO$, $LiClO_4$, $LiIO_4$, $Li_2O$, $LiOH$, $LiOCH_3$, $LiOC_2H_5$, $LiOC_4H_9$, $LiOPh$, $LiOOCOPh$, lithium enolates of the general formula $LiOCR=CR'_2$, where R and R' are aliphatic or aromatic radicals, $LiOSi(CH_3)_3$, $Li(Si(CH_3)_3)_2$, $Li_2CO_3$ or lithium 2,2,6,6-tetramethylpiperidine (LiTMP).

As described above, particular preference amongst these is given to the purely inorganic lithium compounds or the lithium compounds whose usually organic radical is bonded to the lithium atom via inorganic atoms (O, N, Si).

The solvent for carrying out the metallation reaction is, as described above, preferably an ethereal solvent, for example diethyl ether, tetrahydrofuran (THF) or dibutyl ether. However, other polar solvents, such as methyl ethyl ketone and the like, may likewise be used, but also, depending on the hydroxyacetophenone employed, a polar solvents, such as, for example, n-hexane, heptane, benzene, toluene, etc.

It has also been noted that compounds of the formula I can have a stabilising effect on the preparation. When used in corresponding products, the latter are thus also stable for longer and do not change their appearance. In particular, the effectiveness of the ingredients, for example vitamins, is retained even in the case of application over extended periods or extended storage. This is particularly advantageous in the case of compositions for protecting the skin against the effect of UV rays since these cosmetics are exposed to particularly high stresses by UV radiation.

The antioxidant action of the compounds of the formula I can be demonstrated, for example, by means of 2,2-diphenyl-1-picrylhydrazyl (DPPH) assay. 2,2-Diphenyl-1-picrylhydrazyl is a free radical which is stable in solution. The unpaired electron results in a strong absorption band at 515 nm, and the solution has a dark violet color. In the presence of a free-radical scavenger, the electron is paired, the absorption disappears, and the decoloration proceeds stoichiometrically taking into account the electrons taken up. The absorbance is measured in a photometer. The antifree-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which can be considered to be a property of the substance under the given measurement conditions. The substance investigated is compared with a standard (for example tocopherol).

The evaluation is carried out graphically by plotting the test substance/DPPH molar ratio against the percentage decrease in absorbance, and the $EC_{50}$ is determined by reading off at 50%. In addition, the slope of the straight lines in the linear region is determined and the $EC_{50}$ calculated.

The positive effects of compounds of the formula I give rise to their particular suitability for use in cosmetic or pharmaceutical preparations.

The properties of compounds of the formula I should likewise be regarded as positive for use in foods or as food supplements or as functional foods. The further explanations given for foods also apply correspondingly to food supplements and functional foods.

The foods which can be enriched with one or more compounds of the formula I in accordance with the present invention include all materials which are suitable for consumption by animals or consumption by humans, for example vitamins and provitamins thereof, fats, minerals or amino acids. (The foods may be solid, but also liquid, i.e. in the form of a beverage). Foods which can be enriched with one or more compounds of the formula I in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I in accordance with the present invention are corn or cereals from a single plant species and materials produced from plant species of this type, such as, for example, cereal syrup, rye flour, wheat flour or oatbran. Mixtures of foods of this type are also suitable for being enriched with one or more compounds of the formula I in accordance with the present invention, for example multivitamin preparations, mineral mixtures or sweetened juice. As further examples of foods which can be enriched with one or more compounds of the formula I in accordance with the present invention, mention may be made of food preparations, for example prepared cereals, biscuits, mixed drinks, foods prepared especially for children, such as yogurt, diet foods, low-calorie foods or animal feeds.

The foods which can be enriched with one or more compounds of the formula I in accordance with the present invention thus include all edible combinations of carbohydrates, lipids, proteins, inorganic elements, trace elements, vitamins, water or active metabolites of plants and animals.

The foods which can be enriched with one or more compounds of the formula I in accordance with the present invention are preferably administered orally, for example in the form of meals, pills, tablets, capsules, powders, syrup, solutions or suspensions.

The foods according to the invention enriched with one or more compounds of the formula I can be prepared using techniques which are well known to the person skilled in the art.

Due to their action as antioxidants or free-radical scavengers, compounds of the formula I are also suitable as medicament ingredients. Here, they support or replace natural mechanisms which scavenge free radicals in the body. The compounds of the formula I can in some cases be compared in terms of their action with free-radical scavengers such as vitamin C. Compounds of the formula I can be used, for example, for preventative treatment of inflammation and allergies of the skin and in certain cases for preventing certain types of cancer. Compounds of the formula I are particularly suitable for the preparation of a medicament for the treatment of inflammation, allergies and irritation, in particular of the skin. It is furthermore possible to prepare medicaments which act as a vein tonic, as an agent for increasing the strength of blood capillaries, as cuperose inhibitor, as chemical, physical or actinic erythema inhibitor, as agent for the treatment of sensitive skin, as decongestant, as desiccant, as slimming agent, as anti-wrinkle agent, as stimulator for the synthesis of components of the extracellular matrix, as strengthening agent for improving skin elasticity, and as anti-ageing agent. Furthermore, compounds of the formula I which are preferred in this connection exhibit antiallergic and antiinflammatory and antiirritative actions. They are therefore suitable for the preparation of medicaments for the treatment of inflammation or allergic reactions.

The invention furthermore relates, as stated above, to the stabilisation of UV filters. A known and effective class of light-protection filter substances is formed by dibenzoylmethane derivatives. However, it is disadvantageous that these substances are very easily decomposed by UV light, and their protective properties are thus lost. An example of a light-protection filter from this class of compounds which is available on the market is 4-(tert-butyl)-4'-methoxydibenzoylmethane, which has the following structure:

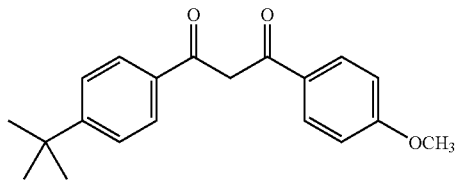

Surprisingly, it has now been found that compounds of the formula I have a stabilising action for dibenzoylmethanes, in particular 4-(tert-butyl)-4-methoxybenzoylmethane. By incorporating mixtures of these compounds into cosmetics, it is now possible to prepare light-protection agents using dibenzoylmethanes which exhibit only a slight reduction in the protective action against UV rays, or none at all, even on extended exposure to the sun, for example during sunbathing for a number of hours.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

| Chemical | Source | Art. No. | Purity |
|---|---|---|---|
| 2',5'-Dihydroxyacetophenone | Merck KGaA | | 98% |
| 2',4'-Dihydroxyacetophenone | Merck KGaA | 818284 | 98% |
| 4-Methoxybenzoyl chloride | Merck KGaA | 820106 | 99% |
| Lithium hydroxide | Merck KGaA | 105691 | 98% |
| D-(+)-alpha-acetobromoglucose | Merck KGaA | 800121 | |
| Tetra-n-butylammonium | Merck KGaA | 818839 | |

-continued

| Chemical | Source | Art. No. | Purity |
|---|---|---|---|
| bromide | | | |
| Sodium hydroxide solution | Merck KGaA | 109137 | 1N |
| Boron tribromide | Merck KGaA | 801063 | 99% |
| Sodium methoxide | Merck KGaA | 806538 | |
| Tetrahydrofuran | Merck KGaA | 108107 | SeccoSolv 0.0075% $H_2O$ |
| Dichloromethane | Merck KGaA | 106049 | ultrapure |
| Hydrochloric acid, fuming | Merck KGaA | 100314 | 37% |
| Acetic acid | Merck KGaA | 100056 | 100% |
| Sulfuric acid | Merck KGaA | 100731 | 95–97% |

Example 1

Preparation of 4'-methoxy-6-hydroxyflavone

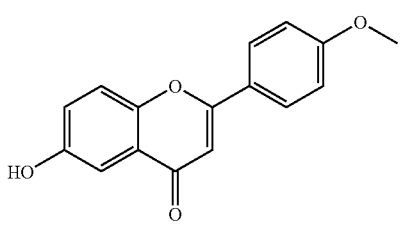

Dry, pulverulent lithium hydroxide (19.7 mmol, 3 equivalents) is added in one portion to a well-stirred solution of 2',5'-dihydroxyacetophenone (6.4 mmol) in dry THF (5 ml) at −78° C. under an argon atmosphere. The reaction mixture is stirred at −78° C. for one hour and subsequently at −1° C. for two hours. After re-cooling to −78° C., a solution of 4-methoxybenzoyl chloride (6.5 mmol) in THF (10 ml) is added in one portion. The mixture is stirred at −78° C. for one hour and at room temperature for 4 hours until the starting material has disappeared. The reaction mixture is emptied onto a mixture of ice (150 g) and concentrated HCl (5 ml) and extracted with dichloromethane (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. under an argon atmosphere for from 30 minutes to one hour. Approximately one third of the acetic acid is stripped off, and the residue is emptied into water. The precipitated product is filtered, washed and dried and recrystallised from methanol to give 4'-methoxy-6-hydroxyflavone. $^1$H NMR (500 MHz, $d^6$-DMSO): δ10.08 (br s, OH), 8.02–7.11 (dm, 4H), 7.63 (d, 1H), 7.35 (d, 1H), 7.26 (d, 1H), 6.86 (s, 1H), 3.88 (s, 3H); $^{13}$C NMR (62.90 MHz, $d^6$-DMSO): δ176.78 (s), 162.23 (s), 161.93 (s), 154.73(s), 149.24 (s), 127.97 (s), 124.14 (s), 123.44 (s), 122.77 (s), 119.61 (s), 114.46 (s), 107.52 (s), 104.44 (s), 55.43 (s); EI-MS (70 eV) m/e (rel. abund.)=268.0735 (100). The product is colorless and exhibits the UV absorption maximum at λ=322 nm with ε=24790 (in 2-propanol) (cf. FIG. 1).

Example 2

Preparation of 4'-methoxy-7-hydroxyflavone

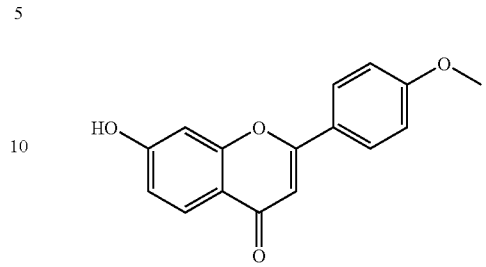

Dry, pulverulent lithium hydroxide (38.7 mmol, 3 equivalents) is added in one portion to a well-stirred solution of 2',4'-dihydroxyacetophenone (12.9 mmol) in dry THF (15 ml) at −78° C. under an argon atmosphere. The reaction mixture is stirred at −78° C. for one hour and subsequently at −10° C. for two hours. After re-cooling it −78° C., a solution of 4-methoxybenzoyl chloride (14.2 mmol) in THF (20 ml) is added in one portion. The mixture is stirred at −78° C. for one hour and at room temperature for 4 hours until the starting material has disappeared. The reaction mixture is emptied onto a mixture of ice (300 g) and concentrated HCl (10 ml) and extracted with dichloromethane (3×50 ml). The solvents are removed from the dried extracts, and the residue is dried under reduced pressure for 24 hours. Glacial acetic acid (100 ml) and sulfuric acid (0.5 ml) are added to the residue, and the mixture is heated at 95–100° C. under an argon atmosphere for from 30 minutes to one hour. Approximately one third of the acetic acid is stripped off, and the residue is emptied into water. The precipitated product is filtered, washed and dried and recrystallised from methanol to give 4'-methoxy-7-hydroxyflavone. $^1$H NMR (250 MHz, $d^6$-DMSO): δ 10.90 (br s, OH), 8.01–7.11 (dm, 4H), 7.87 (d, 1H), 7.00 (d, 1H), 6.93 (d, 1H), 6.81 (s, 1H), 3.86 (s, 3H); $^{13}$C NMR (62.90 MHz, $d^6$-DMSO): δ176.24 (s), 162.58 (s), 162.00 (s), 161.87 (s), 157.39 (s), 127.93 (s), 126.41 (s), 123.42 (s), 116.07 (s), 114.83 (s), 114.48 (s), 105.07 (s), 102.48 (s), 55.46 (s); EI-MS (70 eV) m/e (rel. abund.)=268.07356 (100). The product is beige and exhibits the UV absorption maximum at λ=323 nm with ε=26450 (in 2-propanol) (cf. FIG. 2).

Example 3

Preparation of 4',7-dihydroxyflavone

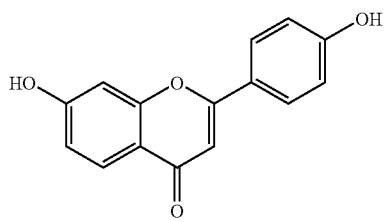

A boron tribromide solution (1.8 ml, 6 equivalents) is added to a well-stirred solution of 4'-methoxy-7-hydroxyflavone (3 mmol) in dichloromethane (50 ml) at −78° C. under an argon atmosphere. When the addition of the boron tribromide solution is complete, the reaction mixture is stirred at room temperature for 24 hours and introduced into an ice/water mixture (300 ml). The product is filtered off and recrystallised from ethanol/water to give 4',7-dihydroxyflavone. $^1$H NMR (300 MHz, d$^6$-DMSO): δ 10.78 (br s, OH), 10.28 (br s, OH), 7.91–6.93 (dm, 4H), 7.87 (d, 1H), 6.98 (d, 1H), 6.72 (s, 1H); $^{13}$C NMR (62.90 MHz, d$^6$-DMSO): δ176.19 (s), 162.43 (s), 162.33 (s), 160.58 (s), 157.27 (s), 128.02 (s), 126.36 (s), 121.68 (s), 116.01 (s), 115.78 (s), 114.67 (s), 104.37(s), 102.48 (s); EI-MS (70 eV) m/e (rel. abund.)=254.24 (100). The product is yellowish and exhibits the UV absorption maximum at λ=329 nm with ε=27960 (in 2-propanol) (cf. FIG. 3).

Example 4

Preparation of 4'-methoxy-7-β-glucosidylflavone

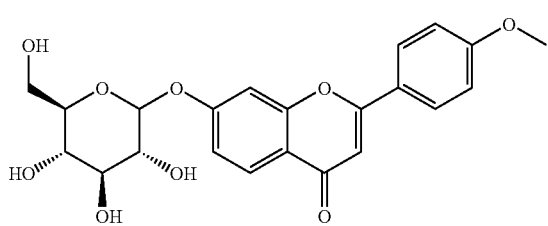

4'-Methoxy-7-hydroxyflavone (3.7 mmol) is stirred for 15 minutes at room temperature in sodium hydroxide solution (50 ml). D-(+)-alpha-aceto-bromoglucose (11 mmol) is dissolved in dichloromethane with tetra-n-butylammonium bromide (5.6 mmol) and added rapidly to the reaction mixture. The reaction mixture is stirred vigorously for 5 hours at room temperature and neutralised using sulfuric acid and water. The product is extracted with ethyl acetate, the organic phases are washed with water and an NaCl solution, and the solvents are removed from the dried extracts to give a yellow crystal slurry. The residue (2.3 g) is dissolved in a solution of sodium methoxide (18.5 mmol) in methanol (150 ml) and stirred at room temperature overnight. The precipitated product is neutralised using glacial acetic acid, pH about 5–6, and cooled in an ice bath for one hour. The solid is filtered off, rinsed with methanol and hexane and dried in a vacuum cabinet at 40° C. and 200 mbar overnight to give 4'-methoxy-7-β-glucosidylflavone (643 mg, 97.7% pure). $^1$H NMR (500 MHz, d$^6$-DMSO): δ 8.05–7.12 (dm, 4H), 7.95 (d, 1H), 7.37 (d, 1H), 7.12 (d, 1H), 6.88 (s, 1H), 5.41 (d, OH), 5.12 (m, OH+1H), 5.05 (d, OH), 4.58 (d, OH), 3.87 (s, 3H), 3.74 (m, 1H), 3.51 (m, 2H), 3.34 (m, 2H), 3.23 (m, 1H); EI-MS (70 eV) m/e (rel. abund.)= 430.1264 (100). The product is slightly yellowish and exhibits the UV absorption maximum at λ=318 nm with ε=37185 (in 2-propanol) (cf. FIG. 4).

Example 5

2-(3',4',5'-trimethoxyphenyl)-6,7-dihydroxy-4-oxo-4H-1-benzopyran

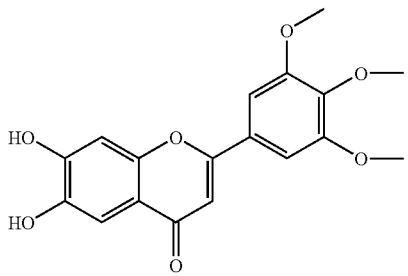

The compound is prepared as described in Example 2.
13C NMR (DMSO-d$_6$, 300 MHz) δ 176.18 (C-4), 161.21 (C-2), 153.14 (C-3' and C-5'), 152.19 (C-7), 150.72 (C-9), 144.52 (C-6), 140.05 (C-4'), 126.90 (C-1'), 115.99 (C-10), 107.46 (C-5), 105.82 (C-8), 103.66 (C-2' and C-6'), 103.29 (C-3), 60.12 (OCH3 on C-4'), 56.18 (OCH3 on C-3' and C-5').

EI-MS m/e (% relative abundance) composition: 344.0896 (100), 343 (1), 330 (8), 329 (31), 328 (1), 315 (7), 314 (6), 302 (2), 301 (8), 286 (2), 284 (2), 273 (5), 271 (4), 269 (3), 258 (2), 255 (1), 243 (3), 242 (2), 241 (4), 215 (2), 213 (1), 195 (1), 193 (1), 192 (8), 187 (4), 177 (11), 162 (2), 158 (8), 153 (9), 152 (4), 149 (6), 143 (7)137 (2), 135 (3), 134 (4), 132 (2), 128 (4), 121 (2), 119 (5), 117 (2), 115 (3), 107 (3), 106 (2), 101 (1), 100 (1).

UV-vis (2-propanol, 1 mg/100 ml) λ$_{max}$ (e) nm: 281 (8267), 324 (16036);

Anal. Calcd for C18H16O7: C, 62.79; H, 4.68; O, 32.53. Found: C, H, O.

Example 6

2-(4'-hydroxyphenyl)-6-hydroxy-4-oxo-4H-1-benzopyran

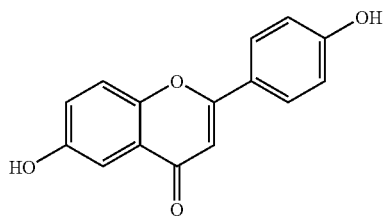

The compound is prepared as described in Example 3.
1H NMR (DMSO-d$_6$, 300 MHz) δ 10.17 (br s, 2H, exchanges with D2O, OH on C-6 and C-4'), 7.4251 (AB, 4H, dA=7.91183 (H-3' and H-5') and dB=6.9318 (H-2' and H-6'), JAB=9.5229), 7.61 (d, 1H, 3J8, 7=9.52, H-8), 7.34 (d, 1H, 4J5, 7=2.64, H-5), 7.18 (dd, 1H, 3J7, 8=9.52, 4J7, 5=2.64, H-7), 6.79 (s, 1H, H-3).

13C NMR (DMSO-d6, 75.47 MHz) d 176.70 (C-4), 162.59 (C-2), 160.68 (C-4'), 154.62 (C-6), 149.14 (C-9), 128.10 (C-2' and C-6'), 124.10 (C-10), 122.62 (C-7), 121.74 (C-1'), 119.53 (C-8), 115.81 (C-3' and C-5'), 107.45 (C-5), 103.80 (C-3).

EI-MS m/e (% relative abundance) composition: 254.0579 (100), 253 (13), 237 (2), 226 (5), 225 (3), 197 (3), 139 (2), 137 (35), 136 (78), 135 (4), 121 (2), 119 (4), 118 (14), 113 (9), 108 (12), 107 (3), 99 (1), 89 (5), 86 (1), 82 (4), 80 (10), 76 (1), 65 (2), 63 (6), 54 (2), 52 (11), 39 (3).

UV-vis (2-propanol, 1 mg/100 ml) $\lambda_{max}$ (e) nm: 228 (23068), 277 (14805), 328 (30971);

Anal. Calcd for C15H10O4: C, 70.86%; H, 3.96%; O, 25.17%. Found: C, 70.4%; H, 4.0%; O, 25.4%.

Formulations of cosmetic preparations which comprise compounds according to Examples 1–4 are indicated by way of example below. In addition, the INCI names of the commercially available compounds are indicated.

UV Pearl, OMC is the preparation with the INCI name: Water (for EU: Aqua), Ethylhexyl Methoxycinnamate, Silica, PVP, Chlorphenesin, BHT; this preparation is commercially available under the name Eusolex®UV Pearl™OMC from Merck KGaA, Darmstadt.

The other UV Pearl products indicated in the tables each have an analogous composition with OMC replaced by the UV filters indicated.

TABLE 1

W/O emulsions (figures in % by weight)

| | 1-1 | 1-2 | 1-3 | 1-4 | 1-5 | 1-6 | 1-7 | 1-8 | 1-9 | 1-10 |
|---|---|---|---|---|---|---|---|---|---|---|
| Titanium dioxide | | 2 | 5 | | | | | | | 3 |
| 4'-Methoxy-7-hydroxyflavone | 5 | 3 | 2 | 1 | 2 | | | | 1 | 1 |
| 4'-Methoxy-6-hydroxyflavone | | | | | | 1 | 2 | 1 | | |
| Zinc oxide | | | | | | | | 5 | 2 | |
| UV-Pearl, OMC | 30 | 15 | 15 | 15 | 15 | 15 | 15 | 15 | 15 | 15 |
| Polyglyceryl 3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium dioxide | 3 | | 2 | | 3 | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| 4',7-Dihydroxyflavone | 5 | 3 | 2 | 5 | 1 | 3 | 7 | 2 |
| Polyglyceryl 3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentaerythrityl Citrate (and) Sorbitan Sesquioleate (and) Cera Alba (and) Aluminium Stearate | | | | | 6 | 6 | 6 | 6 |
| PEG-7 hHdrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerine | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

TABLE 1-continued

| W/O emulsions (figures in % by weight) | | | | | | | | | | | |
|---|---|---|---|---|---|---|---|---|---|---|---|
| | 1-19 | 1-20 | 1-21 | 1-22 | 1-23 | 1-24 | 1-25 | 1-26 | 1-27 | 1-28 | 1-29 |
| Titanium dioxide | | 2 | 5 | | | | | | | 3 | 3 |
| Benzylidene malonate polysiloxane | | | | 1 | | | | | 1 | 1 | |
| Methylene Bis-Benztriazolyl Tetramethylbutylphenol | | | | | | 1 | 2 | 1 | | | 1 |
| Zinc oxide | | | | | | | | 5 | 2 | | |
| UV-Pearl OMC | 5 | 5 | 5 | 5 | 7 | 5 | 5 | 5 | 5 | 5 | 8 |
| UV-Pearl, OCR | | 10 | | | | | | | | | |
| UV-Pearl, EthylhexylDimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| BMDBM | | | | | | | | | | | 2 |
| UV-Pearl OMC, 4-Methylbenzylidene Camphor | 25 | | | | | | | | | | |
| Polyglyceryl 3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

| O/W emulsions, figures in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium dioxide | | 2 | 5 | | | | | | | 3 |
| Methylene Bis-Benztriazolyl Tetramethylbutylphenol | | | | | | 1 | 2 | 1 | | |
| 4'-Methoxy-7-β-glucosidylflavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerine | | | | | | | | | | |
| Water | to 100 | to 100 | to 100 | to 100 | to 100 | to 100 | to 100 | to 100 | to 100 | to 100 |

TABLE 2-continued

O/W emulsions, figures in % by weight

| | 2-11 | 2-12 | 2-13 | 2-14 | 2-15 | 2-16 | 2-17 | 2-18 |
|---|---|---|---|---|---|---|---|---|
| Titanium dioxide | 3 | | 2 | | | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| 4'-Methoxy-7-β-glucosidylflavone | | | | 1 | 2 | | | |
| 4'-Methoxy-6-hydroxyflavone | 1 | 3 | | 2 | | 5 | | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| Zinc oxide | | | 2 | | | | | |
| UV-Pearl, OMC | 15 | 15 | 15 | 30 | 30 | 30 | 15 | 15 |
| 4-Methylbenzyliden Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| Persea Gratissima | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | | 1.8 | | | |
| Glycerine | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | | | | | | | 3 | 3 | | 2 |
| Benzylidene malonate polysiloxane | 1 | 2 | | | | 1 | 1 | | 1 | 0.5 |
| 4'-Methoxy-7-β-glucosidylflavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| Methylene Bis-Benztriazolyl Tetramethylbutylphenol | | | 1 | 2 | 1 | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldecyl Laurate | | | | | | | | | | |
| Cocoglycerides | | | | | | | | | | |
| Tromethamine | | | | | | | | | | |
| Glycerine | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

| Gels, figures in % by weight | | | | | | | | | | |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| a = aqueous gel | | | | | | | | | | |
| Titanium dioxide | | 2 | 5 | | | | | | | 3 |
| 4'-Methoxy-7-β-glucosidylflavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| Benzylidene malonate polysiloxane | | | | 1 | 1 | 2 | | | 1 | 1 |
| Methylene Bis-Benztriazolyl Tetramethylbutylphenol | | 1 | | | | 1 | 2 | 1 | | |
| Zinc oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13–14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 | 3-14 | 3-15 | 3-16 | 3-17 | 3-18 |
|---|---|---|---|---|---|---|---|---|
| a = aqueous gel | | | | a | a | a | a | a |
| Titanium dioxide | 3 | | 2 | | | | | |
| Benzylidene malonate polysiloxane | | 1 | 0.5 | 1 | | 2 | | |
| Methylene Bis-Benztriazolyl Tetramethylbutylphenol | 1 | 1 | 0.5 | | | 1 | 2 | 1 |
| 4'-Methoxy-7-β-glucosidylflavone | | | | 1 | 2 | | | |
| 4'-Methoxy-6-hydroxyflavone | 1 | 3 | | 2 | | 5 | | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| Zinc oxide | | | 2 | | | | | |
| UV-Pearl, Ethylhexyl Methoxycinnamate | 15 | 15 | 15 | 15 | 15 | 15 | 15 | 15 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13–14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

| | 3-19 | 3-20 | 3-21 | 3-22 | 3-23 | 3-24 | 3-25 | 3-26 | 3-27 | 3-28 |
|---|---|---|---|---|---|---|---|---|---|---|
| 4'-Methoxy-7-β-glucosidyl-flavone | | | | 1 | 2 | | | | 1 | 1 |
| 4'-Methoxy-6-hydroxyflavone | 1 | 3 | | 2 | | 5 | | 5 | 2 | |
| 4'-Methoxy-7-hydroxyflavone | 5 | 5 | 5 | 5 | 5 | 5 | 5 | 5 | 5 | 5 |
| 4',7-Dihydroxyflavone | 1 | 5 | 4 | | 6 | | 7 | | 2 | 1 |
| UV-Pearl, OMC | 30 | 30 | 15 | 15 | 15 | 11 | 12 | 15 | 15 | 15 |
| Phenylbenzimidazole Sulfonic Acid | | 4 | 4 | | | | | | | |
| Sorbitol | 5 | 5 | 5 | 5 | 5 | 5 | 5 | 5 | 5 | 5 |
| Carbomer | 1.5 | 1.5 | 1.5 | 1.5 | 1.5 | 1.5 | 1.5 | 1.5 | 1.5 | 1.5 |
| Propylparaben | | | | | | | | | | |
| Methylparaben | 0.15 | 0.15 | 0.15 | 0.15 | 0.15 | 0.15 | 0.15 | 0.15 | 0.15 | 0.15 |

TABLE 3-continued

| Gels, figures in % by weight | | | | | | | | | | |
|---|---|---|---|---|---|---|---|---|---|---|
| Allantoin | 0.2 | 0.2 | 0.2 | 0.2 | 0.2 | 0.2 | 0.2 | 0.2 | 0.2 | 0.2 |
| Tromethamine | 2.4 | 4.2 | 4.2 | 2.4 | 2.4 | 2.4 | 2.4 | 2.4 | 2.4 | 2.4 |
| Water | to 100 | to 100 | to 100 | to 100 | to 100 | to 100 | to 100 | to 100 | to 100 | to 100 |

| | 3-29 | 3-30 | 3-31 | 3-32 | 3-33 | 3-34 | 3-35 | 3-36 |
|---|---|---|---|---|---|---|---|---|
| 4'-Methoxy-7-β-glucosidylflavone | | | | 1 | 2 | | | |
| 4'-Methoxy-6-hydroxyflavone | 1 | 3 | | 2 | | 5 | | 5 |
| 4'-Methoxy-7-hydroxyflavone | 5 | 5 | 5 | 5 | 5 | 5 | 5 | 5 |
| 4',7-Dihydroxyflavone | 1 | 5 | 4 | | 6 | | 7 | |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benzotriazolyl Tetramethylbutylphenol | | 7 | | 6 | | | | |
| UV-Pearl, Ethylhexyl salicylate, BMDBM | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13–14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

The entire disclosure[s] of all applications, patents and publications, cited herein and of corresponding German application No. 102 32 595.2, filed Jul. 18, 2002, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The UV-VIS spectrum was measured on a Varian Cary 100 biospectrophotometer fitted with a heated cell holder (concentration=0.001 g/100 ml of 2-propanol; cell thickness d=1 cm; wavelength range: 200 to 800 nm).

Figure 1:
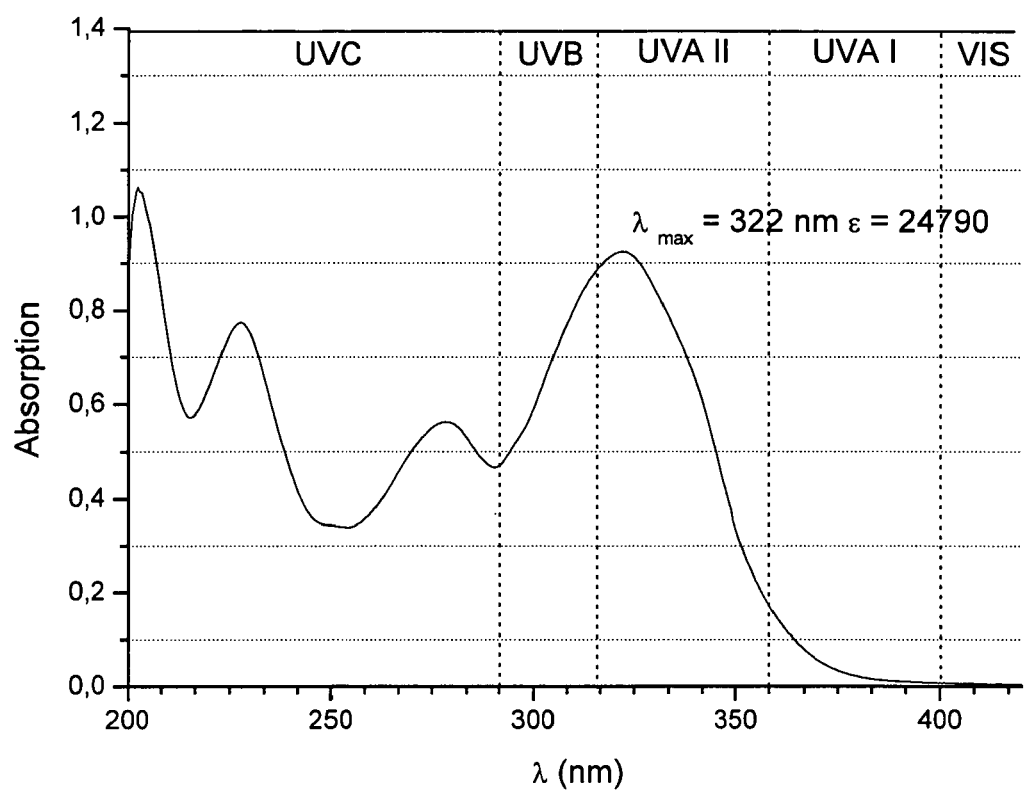
FIG. 1: UV absorption spectrum of 4'-methoxy-6-hydroxyflavone
Figure 2:
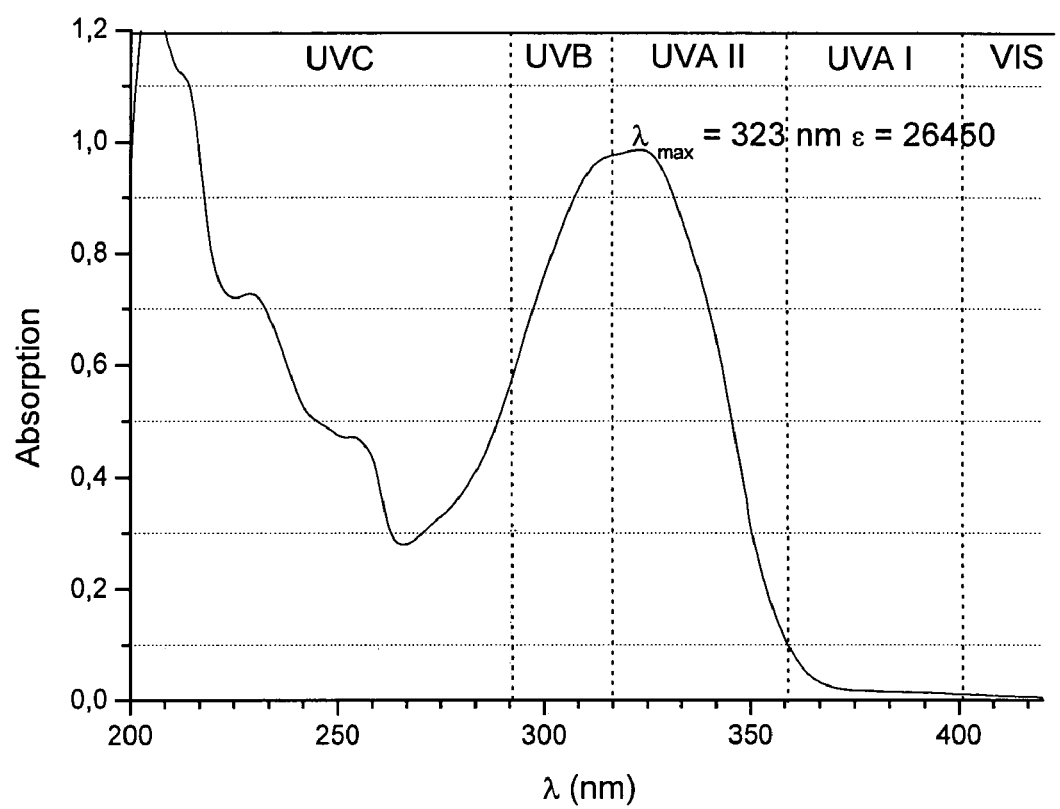

FIG. 2: UV absorption spectrum of 4'-methoxy-7-hydroxyflavone

The UV-VIS spectrum was measured on a Varian Cary 100 biospectrophotometer fitted with a heated cell holder (concentration=0.001 g/100 ml of 2-propanol; cell thickness d=1 cm; wavelength range: 200 to 800 nm).

Figure 3:
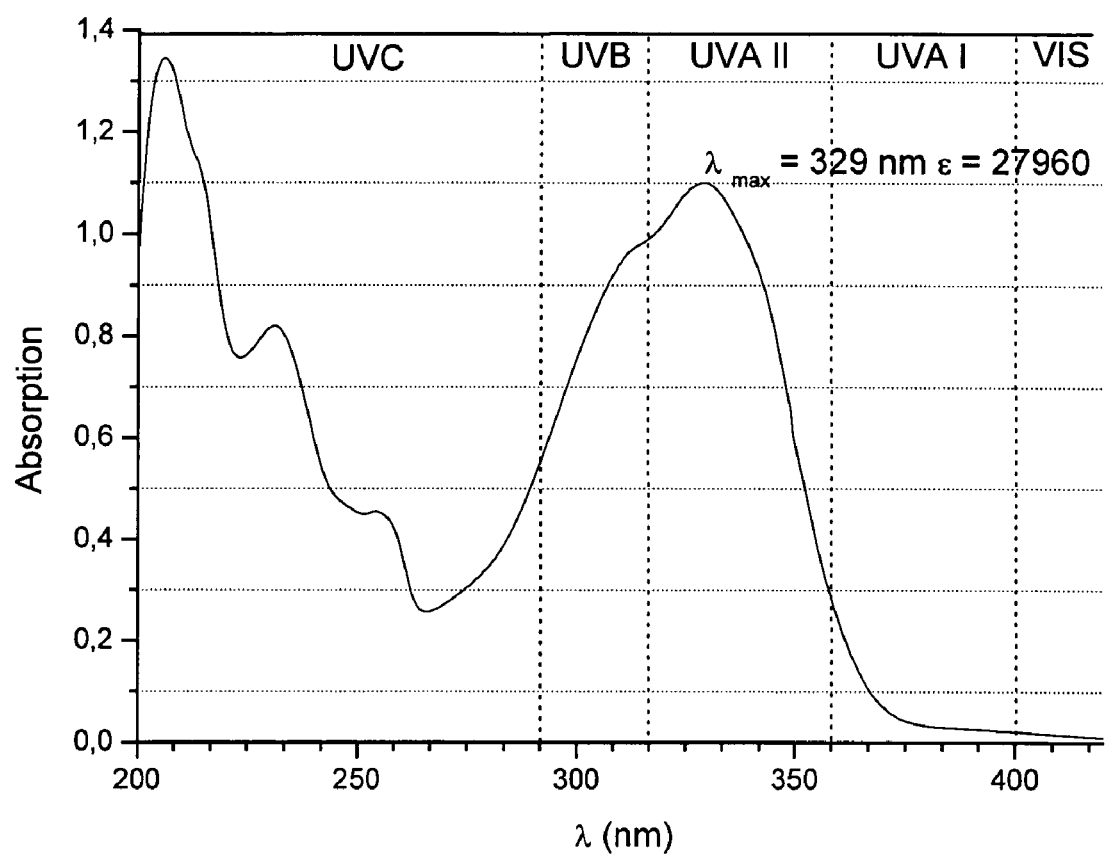

FIG. 3: UV absorption spectrum of 4',7-dihydroxyflavone

The UV-VIS spectrum was measured on a Varian Cary 100 biospectrophotometer fitted with a heated cell holder (concentration=0.001 g/100 ml of 2-propanol; cell thickness d=1 cm; wavelength range: 200 to 800 nm).

Figure 4:
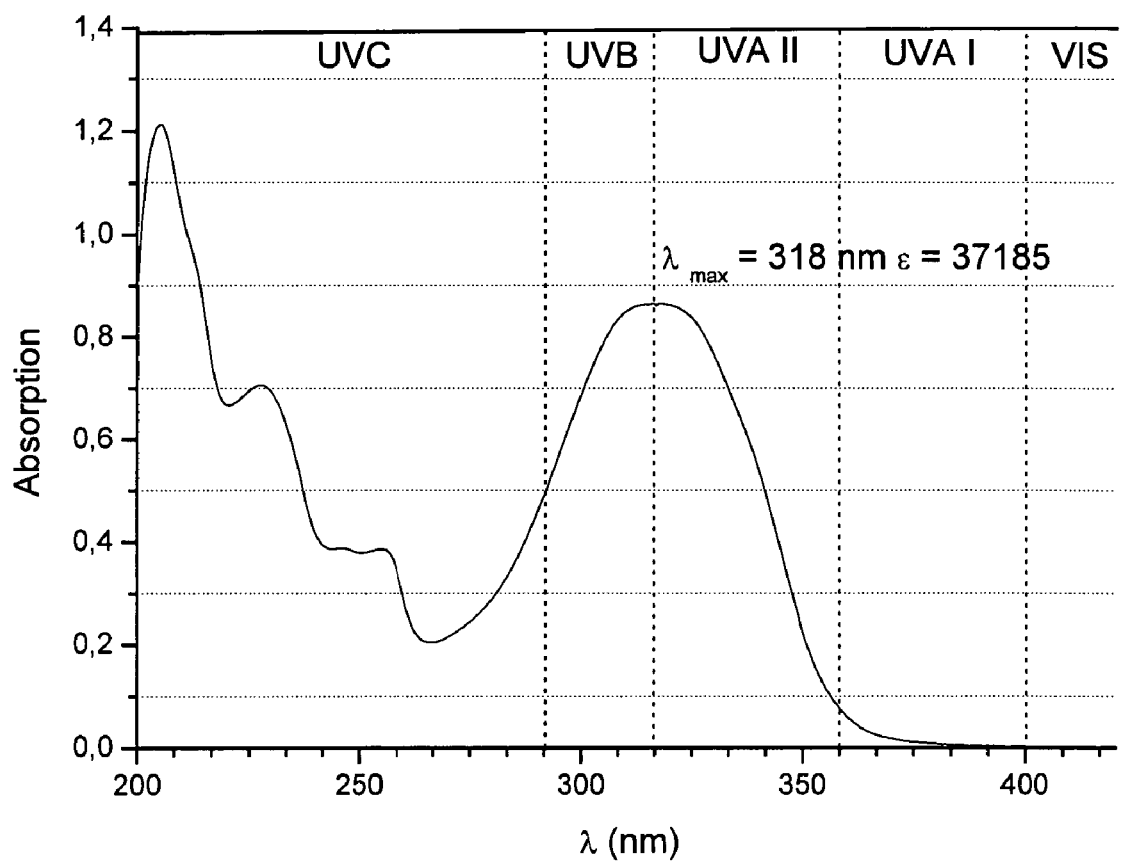

FIG. 4: UV absorption spectrum of 4'-methoxy-7-β-glucosidylflavone

The UV-VIS spectrum was measured on a Varian Cary 100 biospectrophotometer fitted with a heated cell holder (concentration=0.001 g/100 ml of 2-propanol; cell thickness d=1 cm; wavelength range: 200 to 800 nm).

The invention climed is:

1. A method for achieving a light or UV screening effect on the skin of a patient, comprising applying to the skin a compound of formula I

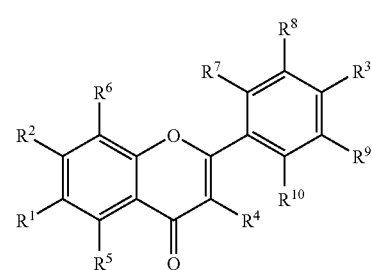

where $R^1$ and $R^2$ are

H or

OR$^{11}$, where each OR$^{11}$ is independently

OH, straight-chain or branched C$_1$- to C$_{20}$-alkoxy, straight-chain or branched C$_3$- to C$_{20}$-alkenyloxy, straight-chain or branched C$_1$- to C$_{20}$-hydroxyalkoxy, where one or more hydroxyl groups is bonded to a primary or secondary carbon atom and alkyl chains of said hydroxyalkoxy moiety optionally being interrupted by oxygen, or a C$_3$- to C$_{10}$-cycloalkoxy group or C$_3$- to C$_{12}$-cycloalkenyloxy group, having rings optionally bridged by —(CH$_2$)$_n$— groups, where n=1 to 3, or mono- and/or oligoglycosyl, with the proviso that at least one of R$^1$ or R$^2$ is OR$^{11}$, R$^3$ is OR$^{11}$, and R$^4$ to R$^7$ and R$^{10}$ are each independently,

H, straight-chain or branched C$_1$- to C$_{20}$-alkyl, straight-chain or branched C$_3$- to C$_{20}$-alkenyl, straight-chain or branched C$_1$- to C$_{20}$-hydroxyalkyl, where the hydroxyl group is bonded to a primary or secondary carbon atom and alkyl chains of said hydroalkyl moieties optionally being interrupted by oxygen, or C$_3$- to C$_{10}$-cycloalkyl groups or C$_3$- to C$_{12}$-cycloalkenyl groups, having rings optionally bridged by —(CH$_2$)$_n$— groups, where n=1 to 3, and R$^8$ and R$^9$ are each independently

H,

OR$^{11}$, straight-chain or branched C$_1$- to C$_{20}$-alkyl, straight-chain or branched C$_3$- to C$_{20}$-alkenyl, straight-chain or branched C$_1$- to C$_{20}$-hydroxyalkyl, where the hydroxyl group is bonded to a primary or secondary carbon atom and alkyl chains of said hydroxyalkyl moieties optionally being interrupted by oxygen, or C$_3$- to C$_{10}$-cycloalkyl or C$_3$- to C$_{12}$-cycloalkenyl, having rings optionally bridged by —(CH$_2$)$_n$— groups, where n=1 to 3.

2. A method according to claim 1 wherein R$^4$ to R$^7$ and R$^{10}$ are H.

3. A method according to claim 1 wherein R$^3$ is

OH or straight-chain or branched C$_1$- to C$_{20}$-alkoxy, or mono- and/or oligoglycosyl, and R$^1$ or R$^2$ are

OH, straight-chain or branched C$_1$- to C$_{20}$-alkoxy or mono- and/or oligoglycosyl.

4. A method according to claim 1, wherein R$^3$ is methoxy, ethoxy or ethylhexyloxy.

5. A method according to claim 1, wherein R$^1$ or R$^2$ is methoxy, ethoxy or ethylhexyloxy.

6. A method according to claim 1, wherein R$^1$ or R$^2$ is glucosyl.

7. A method according to claim 1, wherein compound according to claim 1 wherein R$^3$ is a straight-chain or branched C$_1$- to C$_{20}$-alkoxy group, and R$^8$ and R$^9$ are identical and are H or straight-chain or branched C$_1$- to C$_{20}$-alkoxy.

8. A method according to claim 7, wherein R$^3$ is methoxy, ethoxy or ethylhexyloxy.

9. A method according to claim 7, wherein R$^8$ and R$^9$ is methoxy, ethoxy or ethylhexyloxy.

10. A method according to claim 8, wherein R$^8$ and R$^9$ is methoxy, ethoxy or ethylhexyloxy.

11. A method according to claim 1, wherein at least one of R$^1$ to R$^3$ is OH, and at least one of R$^1$ and R$^2$ is OH.

12. A method according to claim 1, wherein the compound of formula I is applied in the form of a pharmaceutical composition.

13. A method according to claim 12, wherein the pharmaceutical composition is in encapsulated form.

14. A method according to claim 12, wherein the pharmaceutical composition further comprises an additional UV filter.

15. A method according to claim 14, wherein the additional UV filter is 3-(4'-methylbenzylidene)-dl-camphor, 1-(4-tert-butylphenyl)-3-(4-methoxy-phenyl)propane-1,3-dione, 4-isopropyldibenzoylmethane, 2-hydroxy-4-methoxybenzophenone, octyl methoxycinnamate, 3,3,5-trimethyl-cyclohexyl salicylate, 2-ethylhexyl 4-(dimethylamino) benzoate, 2-ethylhexyl 2-cyano-3,3-diphenylacrylate, or 2-phenylbenzimidazole-5-sulfonic acid or a potassium, sodium or triethanolamine salt thereof.

16. A method according to claim 12, wherein the pharmaceutical composition further comprises at least one antioxidant.

17. A method according to claim 12, wherein the pharmaceutical composition comprises a cosmetically or dermatologically suitable excipient.

18. A method according to claim 1, wherein the compound of the formula I is prepared by reacting a 2-hydroxyacetophenone compound with a lithium compound and subsequently a keto compound.

19. A method of stabilizing a UV filter comprising adding thereto a compound of formula I

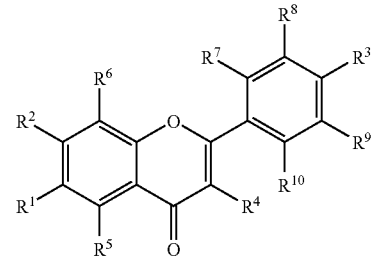

where R$^1$ and R$^2$ are

H or

OR$^{11}$, where each OR$^{11}$ is independently

OH, straight-chain or branched C$_1$- to C$_{20}$-alkoxy, straight-chain or branched C$_3$- to C$_{20}$-alkenyloxy, straight-chain or branched C$_1$- to C$_{20}$-hydroxyalkoxy, where one or more hydroxyl groups is bonded to a primary or secondary carbon atom and alkyl chains of said hydroxyalkoxy moiety optionally being interrupted by oxygen, or a C$_3$- to C$_{10}$-cycloalkoxy group or C$_3$- to C$_{12}$-cycloalkenyloxy group, having rings optionally bridged by —(CH$_2$)$_n$— groups, where n=1 to 3, or mono- and/or oligoglycosyl, with the proviso that at least one of R$^1$ or R$^2$ is OR$^{11}$, R$^3$ is OR$^{11}$, and R$^4$ to R$^7$ and R$^{10}$ are each independently,

H, straight-chain or branched C$_1$- to C$_{20}$-alkyl, straight-chain or branched $C_3$- to $C_{20}$-alkenyl,
straight-chain or branched $C_1$-to $C_{20}$-hydroxyalkyl, where the hydroxyl group is bonded to a primary or secondary carbon atom and alkyl chains of said hydroalkyl moieties optionally being interrupted by oxygen, or
$C_3$- to $C_{10}$-cycloalkyl groups or $C_3$- to $C_{12}$-cycloalkenyl groups, having rings optionally bridged by —$(CH_2)_n$— groups, where n=1 to 3, and $R^8$ and $R^9$ are each independently
H,
$OR^1$, straight-chain or branched $C_1$- to $C_{20}$-alkyl,
straight-chain or branched $C_3$- to $C_{20}$-alkenyl,
straight-chain or branched $C_1$- to $C_{20}$-hydroxyalkyl, where the hydroxyl group is bonded to a primary or secondary carbon atom and alkyl chains of said hydroxyalkyl moieties optionally being interrupted by oxygen, or
$C_3$- to $C_{10}$-cycloalkyl or $C_3$- to $C_{12}$-cycloalkenyl, having rings optionally bridged by —$(CH_2)_n$— groups, where n=1 to 3.

* * * * *